United States Patent [19]
Heinz et al.

[11] Patent Number: 5,437,617
[45] Date of Patent: * Aug. 1, 1995

[54] ELECTROMECHANICAL BACK BRACE APPARATUS

[75] Inventors: Thomas J. Heinz, Flintridge; Tom Walker, Ojai; Eric D. Plambeck, Ventura, all of Calif.

[73] Assignee: Bio Cybernetics International, Pasadena, Calif.

[*] Notice: The portion of the term of this patent subsequent to Sep. 13, 2011 has been disclaimed.

[21] Appl. No.: 297,413

[22] Filed: Aug. 29, 1994

Related U.S. Application Data

[63] Continuation of Ser. No. 197,850, Feb. 17, 1994, abandoned, which is a continuation of Ser. No. 965,305, Oct. 23, 1992, Pat. No. 5,346,461.

[51] Int. Cl.[6] .............................................. A61F 5/00
[52] U.S. Cl. ................................. 602/19; 128/96.1; 128/121.1
[58] Field of Search ............... 128/96.1, 99.1, 100.1, 128/121.1, 125.1, 379, 380, 384, 385; 602/19, 32, 33, 36; 24/32; 182/4

[56] References Cited

U.S. PATENT DOCUMENTS

| | | |
|---|---|---|
| 420,740 | 2/1890 | Sheffield . |
| 2,554,337 | 5/1951 | Lampert . |
| 3,670,320 | 6/1972 | Palmer . |
| 3,926,182 | 12/1975 | Stabholz . |
| 4,007,733 | 2/1977 | Celeste et al. . |
| 4,130,176 | 12/1978 | Paulie . |
| 4,191,949 | 3/1980 | Myers . |
| 4,266,537 | 5/1981 | Bonin, Jr. et al. . |
| 4,365,623 | 12/1982 | Wilhelm et al. . |
| 4,409,969 | 10/1983 | Will . |
| 4,432,356 | 2/1984 | Sarrell et al. . |
| 4,463,750 | 8/1984 | Borschneck . |
| 4,574,789 | 3/1986 | Forster . |
| 4,862,878 | 9/1989 | Davison et al. ............ 2/44 X |
| 5,153,365 | 10/1992 | Chang ........................ 2/311 X |

*Primary Examiner*—Linda C. M. Dvorak
*Attorney, Agent, or Firm*—Nikaido, Marmelstein, Murray & Oram

[57] ABSTRACT

A back brace apparatus is disclosed which has electromechanical mechanism for tightening a brace around the trunk of a patient to a desired tension. The electromechanical mechanism is controllable by the patient to effect predetermined tension settings. A cable and pulley arrangement tightened by a motor provides a mechanical advantage so that the brace may be tightened by a small motor. A microprocessor controls the motor to obtain the desired repeatable tension settings.

13 Claims, 3 Drawing Sheets

ELECTROMECHANICAL BACK BRACE APPARATUS

This application is a continuation of application Ser. No. 08/197,850 filed Feb. 17, 1994, now abandoned, which in turn is a continuation of application Ser. No. 07/965,305 filed Oct. 23, 1992, now U.S. Pat. No. 5,346,461.

BACKGROUND OF THE INVENTION

A common method of alleviating pain and promoting healing in post-operative back surgery patients and those otherwise suffering from back injuries is to stabilize the spine by means of a brace. Such braces typically comprise a corset made of canvas or similar material which can be snugly fitted around the patient's trunk. The back portion of the corset usually has pockets into which are inserted rigid stays for providing vertical support.

Such braces are effective if worn properly and consistently, but most patients have difficulty manually adjusting the brace to a tight enough fit for providing adequate support. This is especially true in the case of post-operative patients who are in pain and lack sufficient strength. Such patient non-compliance obviously reduces the effectiveness of the brace.

Another problem with these types of braces is their inability to adapt as the patient moves from a standing to a sitting position. That is, the patient is required to make any necessary adjustments manually to vary the tension depending on whether standing or sitting. Further, it is extremely difficult to adjust the brace to have exactly the same amount of tension or even to set a particular tension for a particular patient.

SUMMARY OF THE INVENTION

The present invention is a corset-type back brace which is tightened around a patient by a motor which can be computer controlled. The brace comprises two segments linked together by a cable. The two segments can be physically separate pieces or can be portions of the same brace body.

At the free ends of each brace segment is a section of hook-and-loop fastener material for connecting the two free ends when the brace is wrapped around the trunk of a patient. The motor is mounted to one of the segments. The cable is connected at one end to a driven shaft or gear of the motor and to the brace body at the other end so that, as the cable is reeled in by the motor, the brace is cinched tight and tensioned.

In one embodiment, the cable is run through a pulley mounted on the brace segment opposite from the motor, with the fixed end of the cable attached to the same brace segment as the motor to result in a 2:1 mechanical advantage when tightening the brace around a patient's trunk. By mounting a series of pulleys on each brace segment and running the cable through them serially, a greater mechanical advantage may be obtained. This reduces the necessary size of the motor. Additionally, the size of the entire apparatus is reduced leading to a less bulky appearance of the back brace and less discomfort for the patient.

The brace can also comprise a microprocessor mounted on the brace body for controlling the operation of the motor. The microprocessor can be appropriately programmed so that the brace is tightened to a predetermined setting, with separate repeatable settings for sitting and standing positions. The microprocessor can also function as a data collection device for monitoring patient compliance. The microprocessor does not need to be at the position of the motor and can be mounted at any place on the back brace. The microprocessor can be mounted to the brace body using a section of hook-and-loop fastener material.

It is preferable that the back brace be operated by a user interface keypad device. The keypad device can have an LCD readout which indicates relative tightness. The microprocessor may also monitor battery condition and other feedback important to the user and display the same on the readout both for the use of the patient and for the use of a health care professional. The microprocessor can alternatively be mounted in the user interface keypad device remotely from the brace body and be linked to the motor by cable. In such an embodiment, the keypad device can be mountable at any place on the back brace by using a section of hook-and-loop fastener material.

It is a first object of the present invention to provide a back brace which may be tightened around a patient with little physical effort on the part of the patient and yet provide the necessary support.

It is a further object of the invention for the back brace to be capable of being tightened automatically to a predetermined extent, thus ensuring repeatability of patient treatment.

It is still a further object of the present invention to provide a back brace enabling a health care professional to predetermine and subsequently monitor patient treatment.

BRIEF DESCRIPTION OF THE DRAWINGS

Other objects, features, and advantages of the invention will become evident in light of the following detailed description considered in conjunction with the referenced drawings of a preferred exemplary embodiment according to the present invention, wherein.

DETAILED DESCRIPTION OF THE INVENTION

Figure 1:
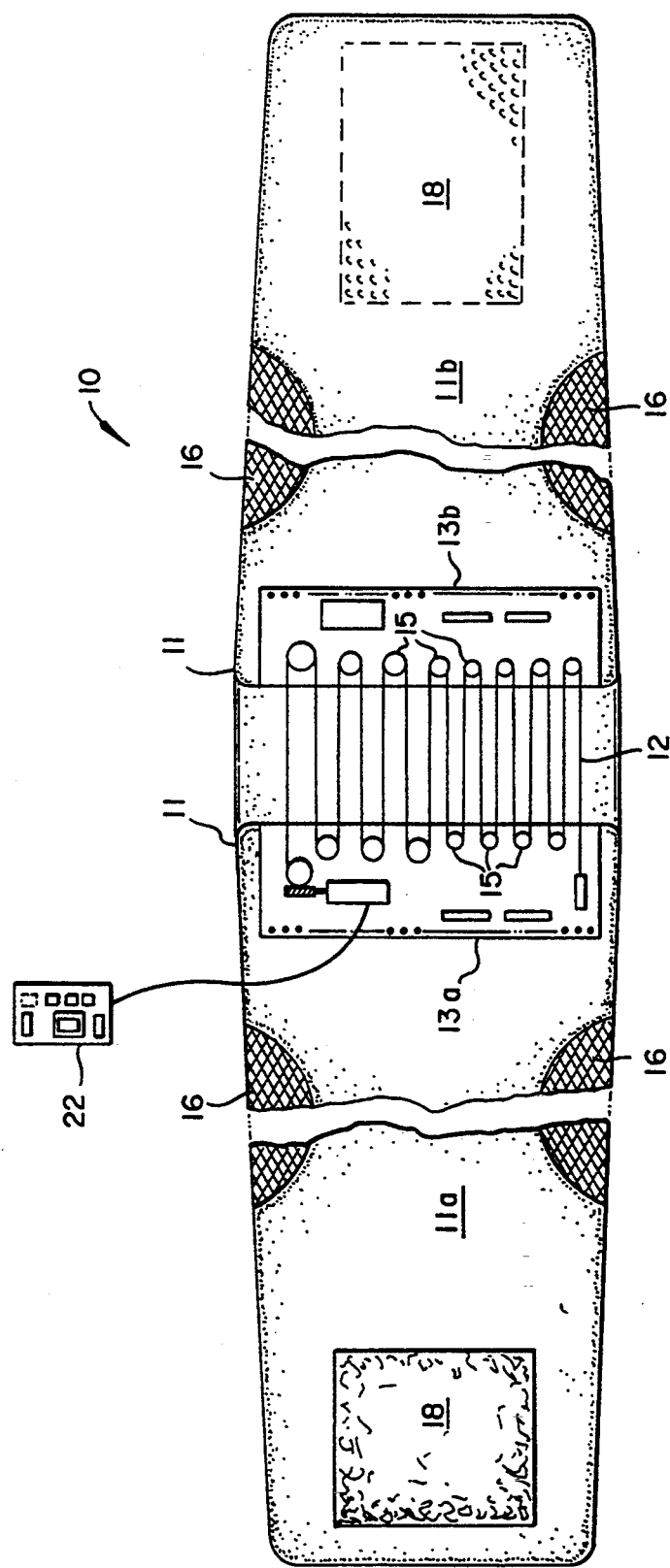
FIG. 1 shows the back brace in accordance with the present invention in its extended position.

FIG. 1 shows a planar view of one side of the back brace apparatus in an extended position. The brace 10 comprises a brace body 11. The brace body 11 is made of canvass or similar fabric and is adapted to be wrapped around the trunk of a patient. A plurality of elastic portions 16 can be provided along upper and lower edges of the brace body for greater patient comfort during use. The brace body 11 is made up of two brace segments 11a and 11b, each having part of the means for automatically tightening the brace. A section of hook-and-loop fastener fabric 18 is mounted on opposite sides of each brace segment at the free ends opposite from the plates described below for securing the two free ends together after the brace is wrapped around the patient's trunk. Such material is capable of withstanding a large amount of shear stress so that the brace 10 may be kept under tension but can be easily peeled away when the apparatus is to be taken off.

The means for automatically tightening the brace can include a cable 12 and a plate 13a or 13b mounted on each brace segment. Each plate 13a or 13b has a series of pulleys 15 mounted on it at staggered positions relative to the other plate. The cable 12 runs serially through the pulleys 15 and is fixed at each end in a manner described more fully below so as to hold the brace segments in position.

The brace segments can be held together at their ends by the cable. Foldover or slip sleeve fabric covers can be provided for the cable and plate portions of the brace. The plates 13 are detachably mounted on the brace segments 11 by section of hook-and-loop fastener fabric 18.

Figure 2:
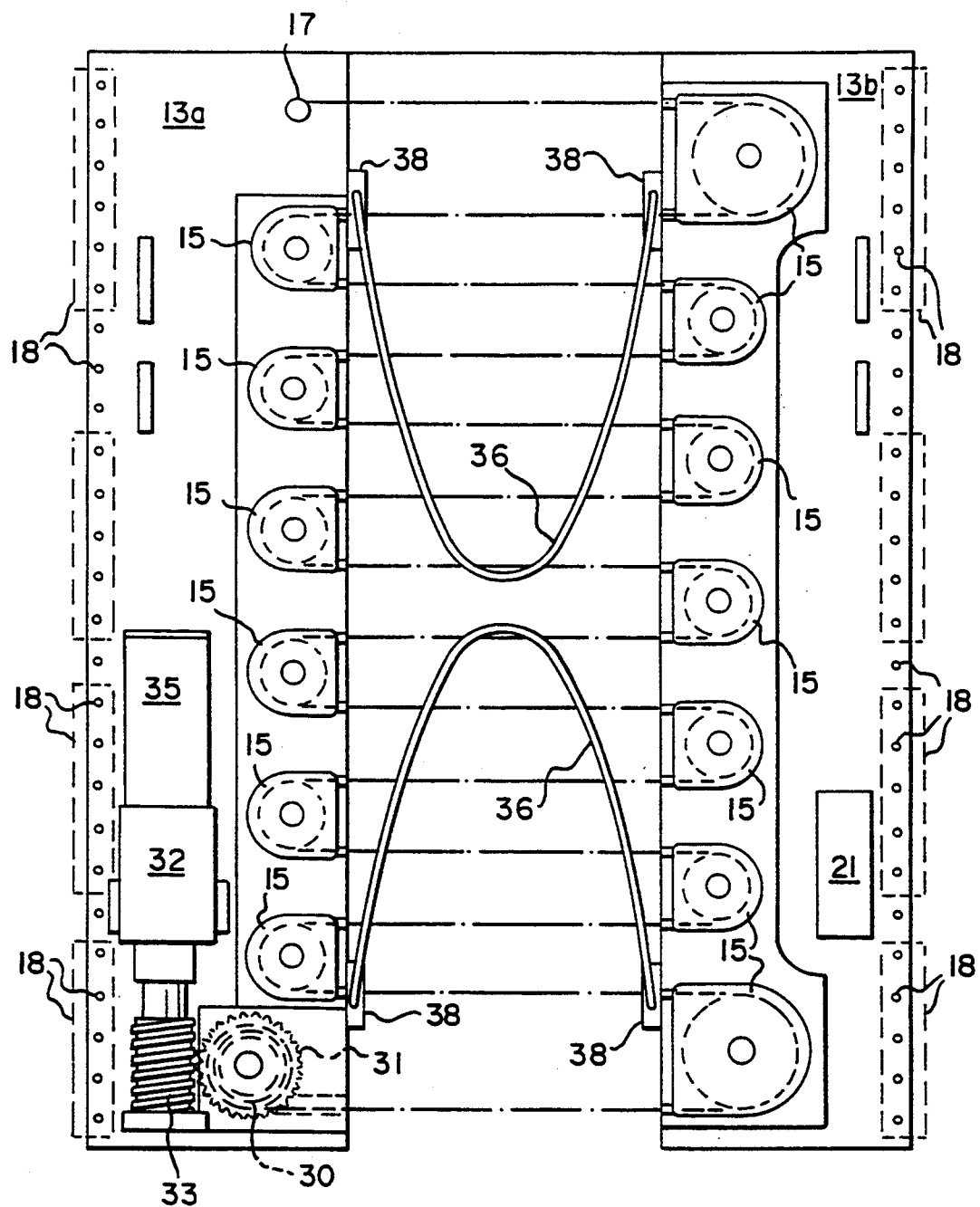
FIG. 2 is a detailed view of the plates.
Figure 3:
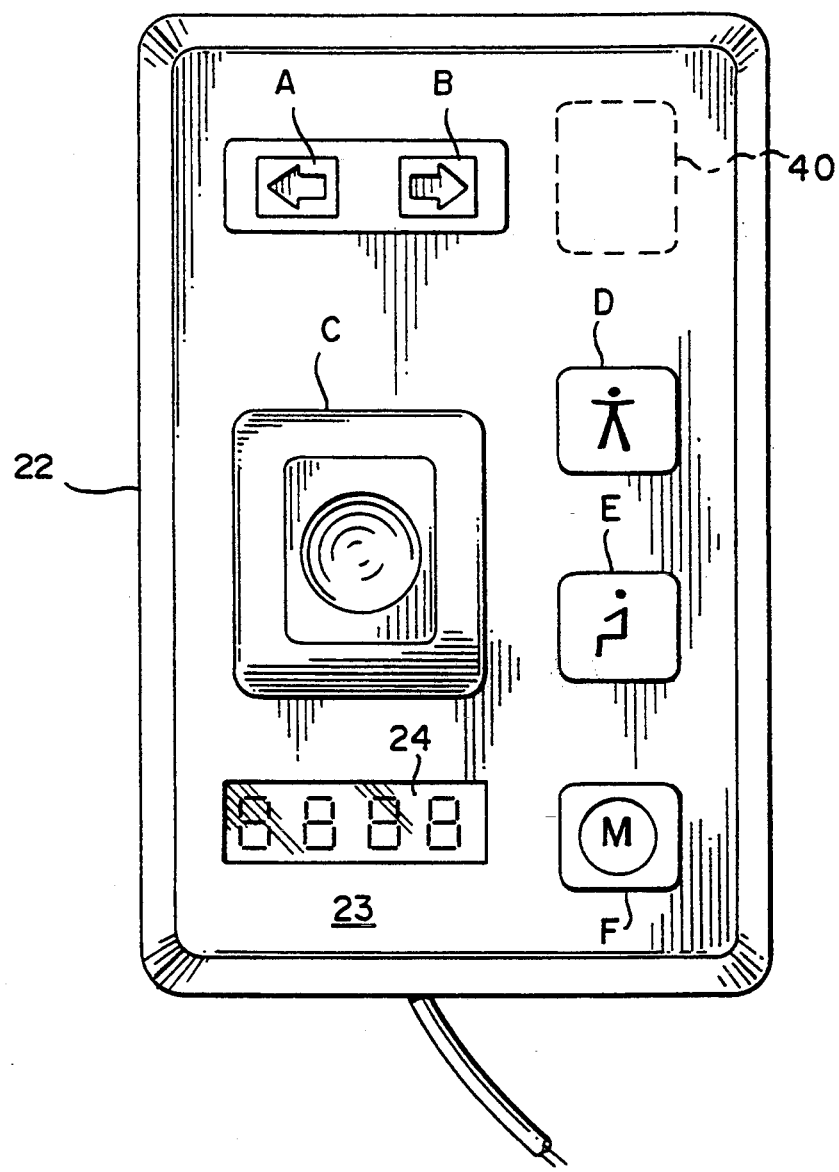
FIG. 3 shows the front of the control module.

FIG. 2 shows part of the means for automatically tightening the brace including the pair of plates 13a and 13b in greater detail. An electric motor 35, a reduction gear train 32, a worm 33, and a worm gear 31 are mounted on plate 13a and are mechanically coupled together so that rotation of motor 35 causes rotation of worm gear 31. A spool 30 is coaxially attached to the worm gear 31 and cable 12 is attached at one end to the spool. The cable 12 is attached at the other end to a fixed point 17 on the plate 13a. Motor 35 thus reels in or out the cable 12 to determine the cable's length. Cable 12 runs through the pulleys 15 on each brace segment in alternating fashion so that shortening of the cable by the motor 35 pulls the two brace segments 11a and 11b closer together and tightens the brace body 11 around the patient's trunk with a mechanical advantage. That mechanical advantage is, of course, determined by the number of pulleys and in the embodiment shown in FIG. 2 is 14:1; with the most preferred embodiment being 16:1.

The means for automatically tightening the brace further includes a means 20 for controlling the operation of the motor. The means for controlling the operation of the motor can include a control module 21 mounted on plate 13a. Alternatively, the means 20 can be included in the keypad interface device 22 described hereinbelow. In a preferred embodiment, the operation of the apparatus is controlled by means of a microprocessor 40 within the module 21 to minimize any power or signal loses.

A plurality of battery brackets (not shown) can also be mounted on the plates together with the necessary wiring for powering the motor. Wires (not shown) running between the plates provide electrical connections for the transmission of power and signals as necessary.

It is preferable that the back brace be operated by a user interface keypad device 22. The keypad interface device 22 can be provided for patient ease of use. A number of buttons which may be accessed by the patient on the front panel 23 of the keypad interface device. Buttons A and B loosen and tighten, respectively, the brace 10 by controlling the length of the cable 12 with the motor 35. In one embodiment during the tightening process, the microprocessor counts the number of rotations made by the motor by optically coupling the motor to the microprocessor's data input circuitry. That number of motor rotations, constitutes a setting for the brace and may be stored for later recall in the microprocessor's memory by the use of the memory button F. If the number of turns of the motor shaft is used as the setting for the tension of the brace, the tension is repeatable for the same patient, but is not presettable to a certain degree of tension.

In another embodiment, the microprocessor monitors and stores the output of a strain gauge either connected within the fabric of the brace or connected to the cable which measures the tension of the brace. The strain gauge can be a spring loaded linear potentiometer attached at the fixed end of the cable.

The preferred embodiment uses monitoring of the motor current as an indirect indicator to measure the tension in the back brace. If the motor 35 is driven by a MOSFET H-bridge, one of the MOSFETs used to drive the motor can be used in conjunction with the resistor below it. An A/D converter could be used to measure the voltage drop across the resistor to indicate the motor current and thus the relative tension on the cable which is proportional to the tension of the brace. The motor current is periodically polled by the microprocessor.

As an example of how the buttons on the keypad device 22 can be used: to store a setting appropriate for the sitting position, button F can be pressed in conjunction with button E. For the standing position, button F can be pressed in conjunction with button D. To recall these settings, the patient would press either button D or E alone which causes the motor 35 to rotate to establish the stored degree of tension. In this way, a patient may easily adjust the setting of brace according to whether they are sitting or standing. A toggle button C is also provided for toggling between the sitting and standing tensions. The keypad device 22 can be attached at any point to the brace and can be connected to the microprocessor by wire. If the keypad device 22 is provided with physical landmarks, the patient could retain it under clothing and using tactile feedback, set and reset the tension of the brace as desired.

The length of the cable 12 is effectively locked when the desired setting is reached simply by the inherent effect of the worm gear and worm together with the reduction gearing.

The keypad device can have an LCD readout 24 which indicates relative tightness and whatever other information that the device is programmed to deliver. The microprocessor may also monitor battery condition and other feedback important to the user and display the same on the readout both for the use of the patient and for the use of a health care professional. The microprocessor can alternatively be mounted in the user interface keypad device remotely from the brace body and be linked to the motor by cable. In such an embodiment, the keypad device can be mountable at any place on the back brace by using a section of hook-and-loop fastener material. It is most preferred that the keypad device be connected to the microprocessor with the minimum of wires. That is, it is most preferred that the keypad device be as autonomous as possible. In this regard, the keypad device has its own power supply and independent microprocessor and communicates with the microprocessor in an asynchronous serial fashion.

An additional interface device can be connected to the microprocessor together with a small peripheral electronic device connectable to a personal computer to enable a health care professional to download data stored in the microprocessor and to upload to the microprocessor the prescribed tension settings. This can simply plug into the keypad device. The use of such an additional interface device enables an interactive brace monitoring system which can empirically derive the optimum usage of the brace. The data downloaded can include a complete hour by hour history of the use of that brace, along with the associated tension. The various connections such as between the microprocessor in the brace and the keypad device, between the additional interface device and the small peripheral electronic device, and between the microprocessor in the brace and the additional interface device may be a direct RF link, or capacitive, inductive or optical nonelectrical (i.e. IR link) connection. It is simply required that the data be transferrable.

Additionally, the microprocessor can be adapted to continuously or periodically sense the tension of the brace. Periodic sensing can be accomplished by momentarily turning the motor on. The motor is turned on only to check the tension vis-a-vis its current consumption. This can be accomplished very quickly without tightening or loosening the brace. Since the microprocessor has available the information of which key was last pressed to set the tension, by periodically checking the motor current consumption/brace tension and comparing it with what it should be in accordance with the last key pressed, it is possible for the microprocessor to determine if the brace has been taken off. That is, if a patient takes the brace off in the fully tightened condition (which is possible since the brace is held in the front by hook-and-loop fasteners), and no loosening of the cable occurs, it will be impossible for the patient to retighten the brace after putting it back on since the cable has been extensively spooled up. The microprocessor would sense this by determining the that the last setting was for a particular tension setting and now that the brace is off of the patient, there is no tension on the cable. When the microprocessor senses that the brace has been taken off, it can unspool the cable so that the brace is automatically ready to be put back on. In such an embodiment, a spring mechanism is added between the two plates and the pulley mountings as the means for loosening the tension setting and unspooling the cable as shown in FIG. 4. The spring mechanism can comprise a pair of piano wire springs 36 engaged in spring brackets 38 and biassing the plates 13 away from each other. It is preferable that the microprocessor poll the current setting and compare it to the last setting desired (by memory of the last key pressed) every 15 seconds. Of course, the timing of the polling can be set to any value desired.

Continuous sensing of the tension level is most desired and with continuous or at least short interval periodic sensing, continuous or semi-continuous adjusting of the tension can be obtained. In this manner, automatic control of the brace can be obtained. The patient can then have the same level of comfort and compliance with the tension required without any additional input.

Although the invention has been described in conjunction with the foregoing specific embodiment, many alternatives, variations, and modifications will be apparent to those of ordinary skill in the art. Those alternatives, variations, and modifications are intended to fall within the scope of the following appended claims.

What is claimed is:

1. A back brace apparatus comprising:
   a brace body adapted to be wrapped around the trunk or a patient, said brace body comprising two segments;
   means at the end of each brace segment for allowing the two ends to be detachably connected together around the patient's trunk; and,
   means for automatically tightening the brace comprising a cable operatively connected to said two segments, a motor operatively connected to apply tension to said cable, and means for controlling said motor, said means for controlling said motor including a microprocessor operatively associated with said motor and programmable to control the motor thereby tightening the brace to a predetermined setting.

2. The back brace apparatus as set forth in claim 1, wherein said brace segments are held together by said cable.

3. The back brace apparatus as set forth in claim 1 wherein the cable is run through at least one pulley mounted on one of the brace segments.

4. The back brace apparatus as set forth in claim 1 further comprising means for storing data including usage time and associated brace tension settings and brace tension, and means for outputting said data for use by a health care professional.

5. The back brace apparatus as set forth in claim 1, further comprising means for automatically loosening the brace tension when the brace is taken off of a user comprising means to periodically sense the tension of the brace, means to store information of a last user input, means to compare tension of the brace with what it should be in accordance with the last user input, and means for spreading the brace segments when the tension sensed is substantially less than what it should be in accordance with the last user input.

6. The back brace apparatus as set forth in claim 5, wherein said means for periodically sensing the tension of the brace comprises means for momentarily turning the motor on and determining load.

7. The back brace apparatus as set forth in claim 1, wherein said means for allowing the two ends of the brace segments to be detachably connected together comprises a section of hook-and-loop fastener material on each of the ends.

8. The back brace apparatus as set forth in claim 1, further comprising means for determining whether user has removed said brace without loosening the tension setting and for operating said means for controlling said motor to loosen said cable, and for means for loosening the tension setting and unspooling the cable.

9. The back brace apparatus as set forth in claim 8, wherein said means for determining whether user has removed said brace without loosening the tension setting and for operating said means for controlling said motor to loosen said cable comprises means for periodically sensing the tension of the brace by momentarily turning the motor and checking the motor current consumption, means for comparing motor current consumption with what it should be in accordance with the last user input, and means for operating said motor to unspool said cable when said motor current consumption is substantially less than what it should be in accordance with the last user input.

10. The back brace apparatus as set forth in claim 8, wherein said means for loosening the tension setting and unspooling the cable comprises spring means for spreading said brace segments apart upon loosening of said cable.

11. The back brace apparatus as set forth in claim 8, wherein said means for determining whether user has removed said brace without loosening the tension setting and for operating said means for controlling said motor to loosen said cable comprises means for periodically sensing the tension of the brace, means to store information of a last user input, means to compare tension of the brace with what it should be in accordance with the last user input, and means for operating said motor to unspool said cable when the tension sensed is substantially less than what it should be in accordance with the last user input.

12. The back brace apparatus as set forth in claim 11, wherein said means for periodically sensing the tension of the brace comprises means for momentarily turning the motor on and determining load.

13. The back brace apparatus as set forth in claim 11, wherein said means for unloosening the tension setting and unspooling the cable comprises spring means for spreading said brace segments apart upon loosening of said cable.

* * * * *